United States Patent [19]

Inukai et al.

[11] 4,374,748

[45] Feb. 22, 1983

[54] 4'-(β-ALKYLOXYETHOXY)-4-CYANOBIPHE-NYL

[75] Inventors: Takashi Inukai; Hideo Sato; Hiromichi Inoue; Masahiro Fukui, all of Yokohama, Japan

[73] Assignee: Chisso Corporation, Osaka, Japan

[21] Appl. No.: 298,769

[22] Filed: Sep. 2, 1981

[30] Foreign Application Priority Data

Sep. 4, 1980 [JP] Japan .............................. 55-122681

[51] Int. Cl.$^3$ ........................... C09K 3/34; C02F 1/13
[52] U.S. Cl. ........................... 252/299.66; 260/465 F; 350/350 R
[58] Field of Search ........... 252/299.5, 299.66, 299.67, 252/299.68, 299.6; 260/465 F, 465 R; 350/350 R

[56] References Cited

U.S. PATENT DOCUMENTS 3,947,375  3/1976  Gray et al. .................. 252/299.66
3,952,046  4/1976  Scherrer et al. ............. 252/299.66
4,005,064  1/1977  Dietrich et al. ............. 252/299.68
4,158,011  6/1979  Inukai et al. ............... 252/299.67

OTHER PUBLICATIONS

Demus, D., "Nonemissive Electro-Optic Displays", Kmetz, A. R., et al, Plenum Press, New York, pp. 83-119, (1976).

Primary Examiner—Teddy S. Gron
Attorney, Agent, or Firm—Wenderoth, Lind & Ponack

[57] ABSTRACT

A novel 4'-(β-alkyloxyethoxy)-4-cyanobiphenyl represented by the general formula:

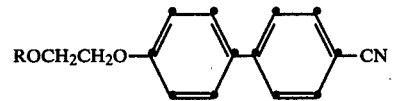

wherein R represents a straight alkyl group having from 1 to 6 carbon atoms, which is useful as one component of liquid crystal composition having positive dielectric anisotropy.

4 Claims, No Drawings

4'-(β-ALKYLOXYETHOXY)-4-CYANOBIPHENYL

The present invention relates to a novel liquid crystal substance having a positive dielectric anisotropy.

It is well known to use a liquid crystal material having a positive dielectric anisotropy for a so-called twisted nematic cell in which nematic liquid crystals having a twisted liquid crystal arrangement are used, utilizing its optical and dielectric anisotropies, or for a colour display element utilizing its guest-host effect.

However, no liquid crystal substance has ever been known which is capable of providing by itself, i.e. as a single liquid crystal compound, various properties such as a liquid crystal temperature range, threshold voltage, response velocity and stability required for the liquid crystal material to be used for the above-mentioned practical purposes. Accordingly, it is common to combine a plurality of liquid crystal compounds or a mixture of them with non-liquid crystal compounds to obtain a liquid crystal composition which can be used for the practical purposes.

It is an object of the present invention to provide a novel liquid crystal compound useful as a component of a liquid crystal composition having a positive dielectric anisotropy and having superior properties for practical use for the above mentioned purposes.

The present invention provides a 4'-(β-alkyloxyethoxy)-4-cyanobiphenyl represented by the general formula:

(I)

wherein R represents a straight alkyl group having from 1 to 6 carbon atoms.

The compounds of the present invention represented by the formula I have a great dielectric anisotropy. Accordingly, it is possible to mix them with a liquid crystal compound having a negative dielectric anisotropy to obtain a liquid crystal composition having a positive dielectric anisotropy. Further, it is possible to add them to a liquid crystal compound having a positive dielectric anisotropy to obtain a composition having a lowered threshold voltage for the electro-optical response.

The compounds of the present invention represented by the formula I may be prepared by any one of the following two methods.

(i) 4'-Bromo-4-hydroxybiphenyl is reacted with copper (I) cyanide to obtain 4'-cyano-4-hydroxybiphenyl (this substance is known), which is then reacted with a β-alkyloxyethylbromide in the presence of an alkaline material.

(ii) 4'-Bromo-4-hydroxybiphenyl is first reacted with a β-alkyloxy-ethylbromide in the presence of an alkaline material to obtain a 4'-(β-alkyloxyethoxy)-4-bromobiphenyl, which is then reacted with copper (I) cyanide.

The above reactions are represented by the following chemical sequence:

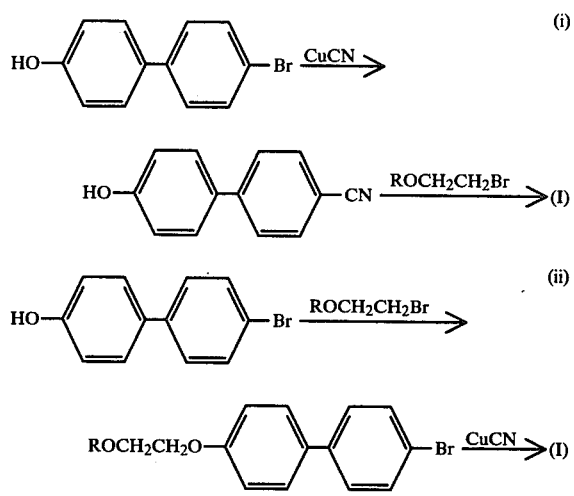

One of the characteristics of the compounds of the formula I according to the present invention is that their dielectric constant anisotropies $\Delta\epsilon$ and $\epsilon_\perp$ (a dielectric constant in the vertical direction to the optical axis) are great. For instance, a mixture composed of one part of a compound of the formula I wherein R is $CH_3$, one part of a compound of the formula I wherein R is $C_2H_5$, and 2 parts of 4'-pentyl-4-cyanobiphenyl, has $\epsilon_\parallel$ (a dielectric constant in the parallel direction to the optical axis) of 23.0 and $\epsilon_\perp$ of 8.2 at room temperature.

4'-Pentyl-4-cyanobiphenyl per se has $\epsilon_\parallel$ of 17.9 and $\epsilon_\perp$ of 6.9, and therefore the difference $\Delta\epsilon$ is calculated as 11.0.

From these values, average dielectric constants of the compounds of the formula I wherein R is $CH_3$ and $C_2H_5$ are assumed to be $\epsilon_\parallel$ being 2.8 and $\epsilon_\perp$ being 9.5, and therefore $\Delta\epsilon$ is assumed to be 18.5. In addition to the great $\Delta\epsilon$ value, it is noticeable that the $\epsilon_\perp$ value is also great. From another system mixture, assumed values of $\epsilon_\parallel$ being 31.3, $\epsilon_\perp$ being 8.1 and $\Delta\epsilon$ being 23.2 have been obtained.

Another characteristic of the compounds of the formula I according to the present invention is that they have a great refractive index anisotropy $\Delta n$. Similar to the above case for $\Delta\epsilon$, a mixture comprising one part of the compound of the formula I wherein R is $CH_3$, one part of the compound of the formula I wherein R is $C_2H_5$ and 2 parts of 4'-pentylcyanobiphenyl, has $n_e$ (a refractive index against extraordinary rays, NaD ray) of 1.746 and $n_o$ (a refractive index against normal rays, NaD ray) of 1.547, and therefore the difference $\Delta n$ is 0.199. From these values and the $n_e$, $n_o$ and $\Delta n$ values (i.e. 1.719, 1.535 and 0.184, respectively) of 4'-pentyl-4-cyanobiphenyl, the difference $\Delta n$ value of the compounds of the formula (I) is assumed to be 0.21 or more. Likewise, from another system mixture, an assumed value of $\Delta n$ being 0.24 has been obtained.

The following Table 1 shows the values of each of $\Delta\epsilon$ and $\Delta n$ of the typical compounds represented by the formula (I) according to the present invention and the known compounds similar to those of the present invention, that is, some examples of each of 4'-alkyl-4-cyanobiphenyl and 4'-alkyloxy-4-cyanobiphenyl.

TABLE 1

| Classification | 4'-substituent | $\Delta\epsilon$* | $\Delta\eta$* | Remarks |
|---|---|---|---|---|
| Compound of | $C_2H_5OCH_2CH_2O$ | 18.0 | ≳0.21 | R represents |

TABLE 1-continued

| Classification | 4'-substituent | Δε* | Δη* | Remarks |
|---|---|---|---|---|
| the present invention | C$_3$H$_7$OCH$_2$CH$_2$O | 18.0 | ≳0.21 | C$_2$H$_5$ in the formula (I) R represents C$_3$H$_7$ in the formula (I) |
| Known compounds | n-C$_5$H$_{11}$ | 11.0 | 0.184 | |
| | n-C$_7$H$_{15}$ | 10.7 | 0.160 | |
| | n-C$_5$H$_{11}$O | 12.0 | 0.193 (50° C.) | |
| | n-C$_8$H$_{17}$O | 10.0 | 0.195 (50° C.) | |

*Unless otherwise specified, there are shown the data at room temperature.

As apparent from the above Table 1, both the data of Δε and Δn of the compounds of the present invention are greater than those of the known compounds.

Further, the compounds of the formula I have a relatively low melting point except for the one with R being CH$_3$ which has slightly too high a melting point, and accordingly they have good compatibility with various known liquid crystal materials and are extremely useful for a combined use with other liquid crystal materials.

The present invention will be illustrated more particularly by the following examples with reference to the preparation and the use of the compounds of the present invention, but the invention is of course not limited only to those examples.

EXAMPLE 1

Preparation of 4'-(β-propyloxyethoxy)-4-cyanobiphenyl

[the above mentioned method (ii)]

70 g of 4'-bromo-4-hydroxybiphenyl, 12 g of sodium hydroxide and 300 ml of 95% ethyl alcohol were charged in a flask. To the mixture were added drop by drop under reflux, 50 g of β-propyloxyethylbromide while stirring for 20 minutes. After the dropwise addition, the mixture was heated and stirred under reflux for 5 hours. About 150 ml of ethyl alcohol were distilled off. After cooling, 300 ml of water were added to the residue. The deposited product was collected by filtration under suction, followed by recrystallizing from 95% ethyl alcohol. There were thus obtained 46 g of 4'-(β-propyloxyethoxy)-4-bromobiphenyl as colourless crystals. The product had a melting point of from 102° to 103° C. 40 g (0.119 mole) of the product were placed, together with 12.8 g (0.07 mole) of copper (I) cyanide and 200 ml of N-methyl-2-pyrrolidone in a three necked flask. The mixture was heated, and a part of N-methyl-2-pyrrolidone was distilled off until the temperature became 210° C. While preventing an entry of moisture, the heating was continued under reflux for 4 hours, whereby about a half of N-methyl-pyrrolidone was distilled off. After cooling, 200 ml of toluene were added to the residue. To the mixture were added an aqueous solution prepared from 24 g of iron (II) chloride hexahydrate, 4 ml of concentrated hydrochloric acid and 160 ml of water. The resulting mixture was stirred at about 65° C. for one hour. The reaction solution was then allowed to separate. The toluene layer was washed in turn with 6 N hydrochloric acid, 2 N sodium hydroxide solution and water.

Toluene was distilled off, and the remainder was subjected to a distillation under reduced pressure, to obtain a fraction having a boiling point of from 213° to 216° C./3 mmHg; there were thus obtained 27.2 g of 4'-(β-propyloxyethoxy)-4-cyanobiphenyl as the desired product. This product was still contaminated with a small amount of impurities. Therefore, it was further dissolved in toluene, and the solution was passed through a chromatographic column filled with active alumina for decolourization. After the removal of toluene by distillation, the product was recrystallized twice from ethyl alcohol to obtain a refined product. The refined product had a melting point of from 34.0° to 34.5° C., and a N-I point of 2.5° C. (monotropic). Further, the elemental analysis of this product corresponded sharp to the calculated values for the assumed formula C$_{18}$H$_{19}$O$_2$N as follows:

| | C | H |
|---|---|---|
| Found (%) | 76.4 | 6.9 |
| Calculated (%) | 76.84 | 6.81 |

EXAMPLE 2

In the same manner as in Example 1 except that the same mole of β-ethoxyethylbromide was used in place of β-propyloxyethylbromide, 4'-(β-ethoxyethoxy)-4-cyanobiphenyl was obtained. The melting point of the product was 66° C. It was impossible to directly measure the N-I point of the product alone. However, the N-I point was found to be 8.5° C. as extrapolated from the N-I point of the mixture with 4'-pentyl-4-cyanobiphenyl.

Further, the melting point of the intermediate, i.e. 4'-(β-ethoxyethoxy)-4-bromobiphenyl was from 109° to 110° C.

EXAMPLE 3

Preparation of 4'-(β-methoxyethoxy)-4-cyanobiphenyl

[the above mentioned method (i)]

60 g of 4'-cyano-4-hydroxy-biphenyl was dissolved in 200 ml of ethyl alcohol, and the solution was heated and stirred. To the solution were further added 12.3 g of sodium hydroxide, 20 ml of water and 100 ml of ethyl alcohol. To the solution were gradually added 43 g of β-methoxyethylbromide for 10 minutes. The mixture was stirred for 3 hours under reflux. After the removal of ethyl alcohol, 200 ml of toluene and 200 ml of water were added followed by stirring. The solution was filtered to remove solid materials. The toluene layer was washed with water, and thereafter toluene was distilled off. The remainder was subjected to a distillation under reduced pressure, to obtain 45.3 g of a distillate having a boiling point of from 198° to 203° C./3 mmHg. This product was the desired 4'-(β-methoxyethoxy)-4-cyanobiphenyl. As the product is still impure the preduct was dissolved in toluene and the solution was subjected to a chromatography with a column of active alumina for decolourization. The product was further recrystallized twice from ethyl alcohol to obtain a refined product which had a melting point of from 88.5° to 89.2° C. and a N-I point of 62.5° C. (monotropic). Elemental analysis of the product corresponded sharp with the calculated values for the assumed formula C$_{16}$H$_{15}$O$_2$N as follows:

| | H | C |
|---|---|---|
| Found (%) | 75.6 | 6.0 |

|  | H | C |
|---|---|---|
| Calculated (%) | 75.87 | 5.97 |

EXAMPLES 4, 5, 6 and 7

In the same manner as in Example 3 except that β-ethoxyethylbromide, β-butoxyethylbromide, β-pentyloxyethylbromide, or β-hexyloxyethylbromide was used in place of β-methoxyethylbromide, there were obtained 4'-(β-ethoxyethoxy)-4-cyanobiphenyl (Example 4: the melting point, etc. were the same as in Example 2), 4'-(β-butoxyethoxy)-4-cyanobiphenyl [Example 5: the melting point was from 15.3° to 16.2° C., and the N-I point was −9° C. (monotropic)], 4'-(β-pentyloxyethoxy)-4-cyanobiphenyl [Example 6: the melting point was 19.8° to 20.3° C., and the N-I point was −2.3° C. (monotropic)] or 4'-(β-hexyloxyethoxy)-4-cyanobiphenyl (Example 7: the melting point (C-N point) was from 10.5° to 11.0° C. and the N-I point was 19° C.), respectively.

EXAMPLE 8 (use example 1)

| 4-Propylcyclohexylbenzonitrille (Merck Co. Product S-1103 PCH) | 24 parts |
|---|---|
| 4-Pentylcyclohexylbenzonitrile (Merck Co. Product S-1114 PCH) | 36 parts |
| 4-Heptylcyclohexylbenzontrile (Merck Co. Product S-1115 PCH) | 15 parts |
| 4'-(β-Propyloxyethoxy)-4-cyanobiphenyl (A compound of the formula I wherein R is C₃H₇) | 15 parts |

A liquid crystal composition having the above components had a freezing point of −20° C. or lower, a clear point of 46.7° C., ε∥ of 16.5, ε⊥ of 5.4, and accordingly the difference Δε is calculated as 11.1. Further, its Δn was 0.14. In a twisted nematic cell (TN cell) wherein this liquid crystal composition was used, the threshold voltage in the electrooptical response was 1.38 V, and its saturated voltage was 1.96 V. In the comparative composition free from the compound of the formula I of the present invention i.e. the composition comprising the remaining three components, the threshold voltage was 1.53 V, the saturated voltage was 2.12 V, and Δn was 0.12.

EXAMPLE 9 (use example 2)

| p-Cyanophenyl p-ethylbenzoate | 11 parts |
|---|---|
| p-Butoxyphenyl trans-4-propylcyclohexane carboxylate | 15 parts |
| p-Ethoxyphenyl trans-4-butylcyclohexane carboxylate | 15 parts |
| p-Ethoxyphenyl trans-4-propylcyclohexane carboxylate | 10 parts |
| p-Hexyloxyphenyl trans-4-butyl-cyclohexane carboxylate | 15 parts |
| p-Methoxtphenyl trans-4-pentyl-cyclohexane carboxtlate | 12 parts |
| 4'-Cyano-4-biphenyl p-(trans-4-heptylcyclohexyl) benzoate | 5 parts |
| 4'-(β-propyloxyethoxy)-4-cyanobiphenyl (Compound of the formula I wherein R represents C₃H₇) | 17 parts |

A liquid crystal composition having the above components had a freezing point of −20° C. or lower, a clear point of 66.5° C., ε∥ of 12.8, ε⊥ of 5.8, and accordingly difference Δε is calculated as 7.0, and Δn of 0.123. In a TN cell wherein this liquid crystal composition was sealed, the threshold voltage in the electrooptical response was 1.63 V, the saturated voltage was 2.16 V, and the 50% response voltage was 1.84 V. The threshold voltage series in the ratio of −6.3 mV/°C., in accordance with the temperature change.

What is claimed is:

1. A 4'-(β-alkyloxyethoxy)-4-cyanobiphenyl represented by the general formula:

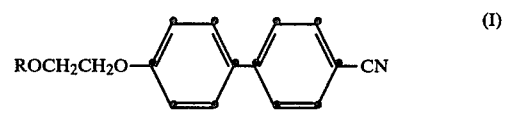

wherein R represents a straight alkyl group having from 1 to 6 carbon atoms.

2. The compound according to claim 1, wherein R in the formula (I) represents propyl group.

3. The compound according to claim 1, wherein R in the formula (I) represents ethyl group.

4. A liquid crystal material for a display cell comprising as an essential component a 4'-(β-alkyloxyethoxy)-4-cyanobiphenyl represented by the general formula:

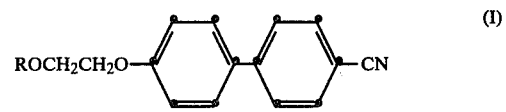

wherein R represents a straight alkyl group having from 1 to 6 carbon atoms.

* * * * *